(12) United States Patent
Yamamoto

(10) Patent No.: US 8,663,115 B2
(45) Date of Patent: Mar. 4, 2014

(54) ULTRASOUND PROBE AND ULTRASOUND DIAGNOSTIC APPARATUS

(75) Inventor: Katsuya Yamamoto, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 11 days.

(21) Appl. No.: 13/362,577

(22) Filed: Jan. 31, 2012

(65) Prior Publication Data
US 2012/0220871 A1    Aug. 30, 2012

(30) Foreign Application Priority Data
Feb. 28, 2011    (JP) ................. 2011-041447

(51) Int. Cl.
A61B 8/00    (2006.01)
A61B 8/14    (2006.01)

(52) U.S. Cl.
USPC ............ 600/443; 600/440; 600/447; 600/441

(58) Field of Classification Search
None
See application file for complete search history.

(56) References Cited

U.S. PATENT DOCUMENTS

| | | | |
|---|---|---|---|
| 4,958,327 A * | 9/1990 | Saitoh et al. | 367/7 |
| 6,027,447 A * | 2/2000 | Li | 600/447 |
| 2010/0076312 A1 | 3/2010 | Katsuyama | |

FOREIGN PATENT DOCUMENTS

| | | |
|---|---|---|
| JP | 8-317926 A | 12/1996 |
| JP | 2002034986 A | 2/2002 |
| JP | 2010-99452 A | 5/2010 |
| JP | 2010264124 A | 11/2010 |

OTHER PUBLICATIONS

Notification of Reasons for Refusal, dated Jan. 29, 2013, issued in corresponding JP Application No. 2011-041447, 5 pages in English and Japanese.

* cited by examiner

Primary Examiner — Long V. Le
Assistant Examiner — Farshad Negarestan
(74) Attorney, Agent, or Firm — Sughrue Mion, PLLC

(57) ABSTRACT

An ultrasound probe includes a transducer array for a B-mode image which transmits and receives an ultrasonic beam for a B-mode image, and a transducer array for sound speed measurement which is laminated and formed above the transducer array for a B-mode image and receives an ultrasonic beam for sound speed measurement.

12 Claims, 3 Drawing Sheets

FIG. 2
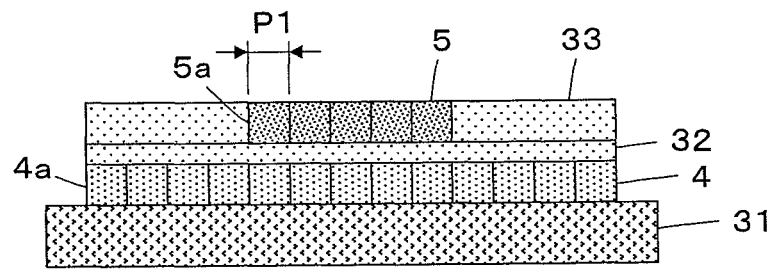
FIG. 3A          FIG. 3B
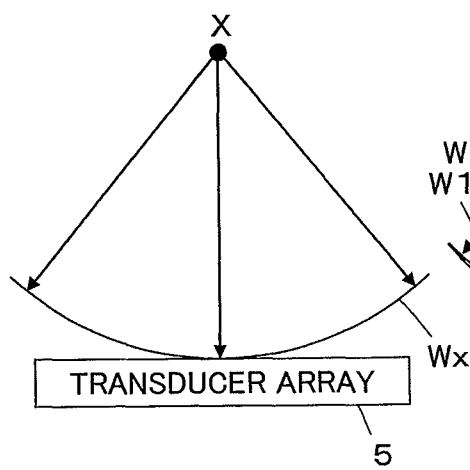 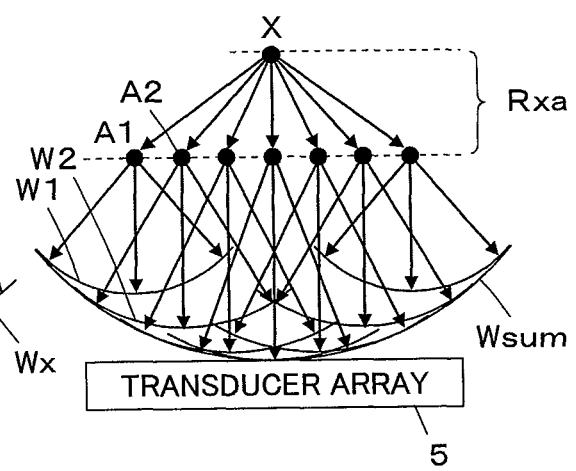
FIG. 4
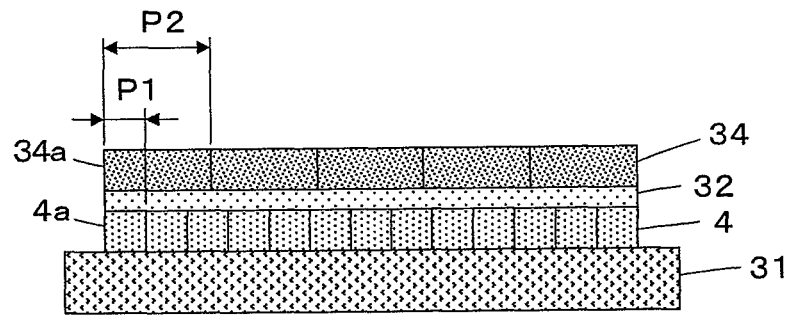

ULTRASOUND PROBE AND ULTRASOUND DIAGNOSTIC APPARATUS

BACKGROUND OF THE INVENTION

The present invention relates to an ultrasound probe and an ultrasound diagnostic apparatus, and in particular, to an ultrasound probe and an ultrasound diagnostic apparatus for performing both production of a B-mode image and production of a sound speed map.

An ultrasound diagnostic apparatus using an ultrasound image has hitherto been put into practical use in the field of medicine. In general, this type of ultrasound diagnostic apparatus has an ultrasound probe equipped with a transducer array and an apparatus body connected to the ultrasound probe. An ultrasonic beam is transmitted from the ultrasound probe toward a subject, an ultrasonic echo from the subject is received by the ultrasound probe, and the reception signal is electrically processed by the apparatus body to produce an ultrasound image.

In recent years, in order to diagnose a region under diagnosis in the subject with greater precision, the sound speed in the region under diagnosis is measured.

For example, JP 2010-99452 A describes an ultrasound diagnostic apparatus which sets a plurality of lattice points in the vicinity of the region under diagnosis, and a local sound speed value is calculated on the basis of reception data obtained by transmitting and receiving an ultrasonic beam for each lattice point.

In the apparatus described in JP 2010-99452 A, the ultrasonic beam is transmitted from the ultrasound probe toward the subject and received by the ultrasound probe to calculate the local sound speed value in the region under diagnosis, making it possible to display information of the local sound speed on the B-mode image in an overlapping manner. If a sound speed map which represents the distribution of the local sound speed values at a plurality of points in a predetermined region is produced and displayed along with a B-mode image, it is effective to diagnose the region under diagnosis.

In order to calculate a more accurate local sound speed value, an ultrasonic beam is transmitted such that, compared to production of a B-mode image, a transmission focus is targeted to each of a plurality of lattice points set in the vicinity of the region under diagnosis, and an ultrasonic echo is transmitted through a wide opening. For this reason, it is preferable that a transducer array which is used for sound speed map production be provided separately from a transducer array which is used for B-mode image production.

However, if both a transducer array for a B-mode image and a transducer array for a sound speed map are disposed in a subject abutment portion of the ultrasound probe, a subject abutment portion has a large area, and operational performance when the subject abutment portion of the ultrasound probe is pressed against the body surface of the subject may be deteriorated.

SUMMARY OF THE INVENTION

The invention has been finalized in order to solve the drawbacks in the related art, and an object of the invention is to provide an ultrasound probe and an ultrasound diagnostic apparatus capable of performing both production of a B-mode image and production of an accurate sound speed map with satisfactory operational performance.

An ultrasound probe according to the present invention comprises:
a transducer array for a B-mode image which transmits and receives an ultrasonic beam for a B-mode image; and
a transducer array for sound speed measurement which is laminated and formed above the transducer array for a B-mode image and receives an ultrasonic beam for sound speed measurement.

An ultrasound diagnostic apparatus according to the present invention comprises:
the above-mentioned ultrasound probe;
an image producer which produces a B-mode image on the basis of reception data for a B-mode image obtained by the reception circuit; and
a sound speed map producer which produces a sound speed map on the basis of reception data for sound speed measurement obtained by the reception circuit.

BRIEF DESCRIPTION OF THE DRAWINGS

FIG. 2 is a sectional view showing the structure of a laminated transducer array which is used in the ultrasound probe according to Embodiment 1.

FIG. 3 is a diagram schematically showing the principle of sound speed calculation in Embodiment 1.

FIG. 4 is a sectional view showing the structure of a laminated transducer array which is used in an ultrasound probe according to Embodiment 2.

DETAILED DESCRIPTION OF THE INVENTION

Hereinafter, embodiments of the invention will be described with reference to the accompanying drawings.

Embodiment 1

Figure 1:
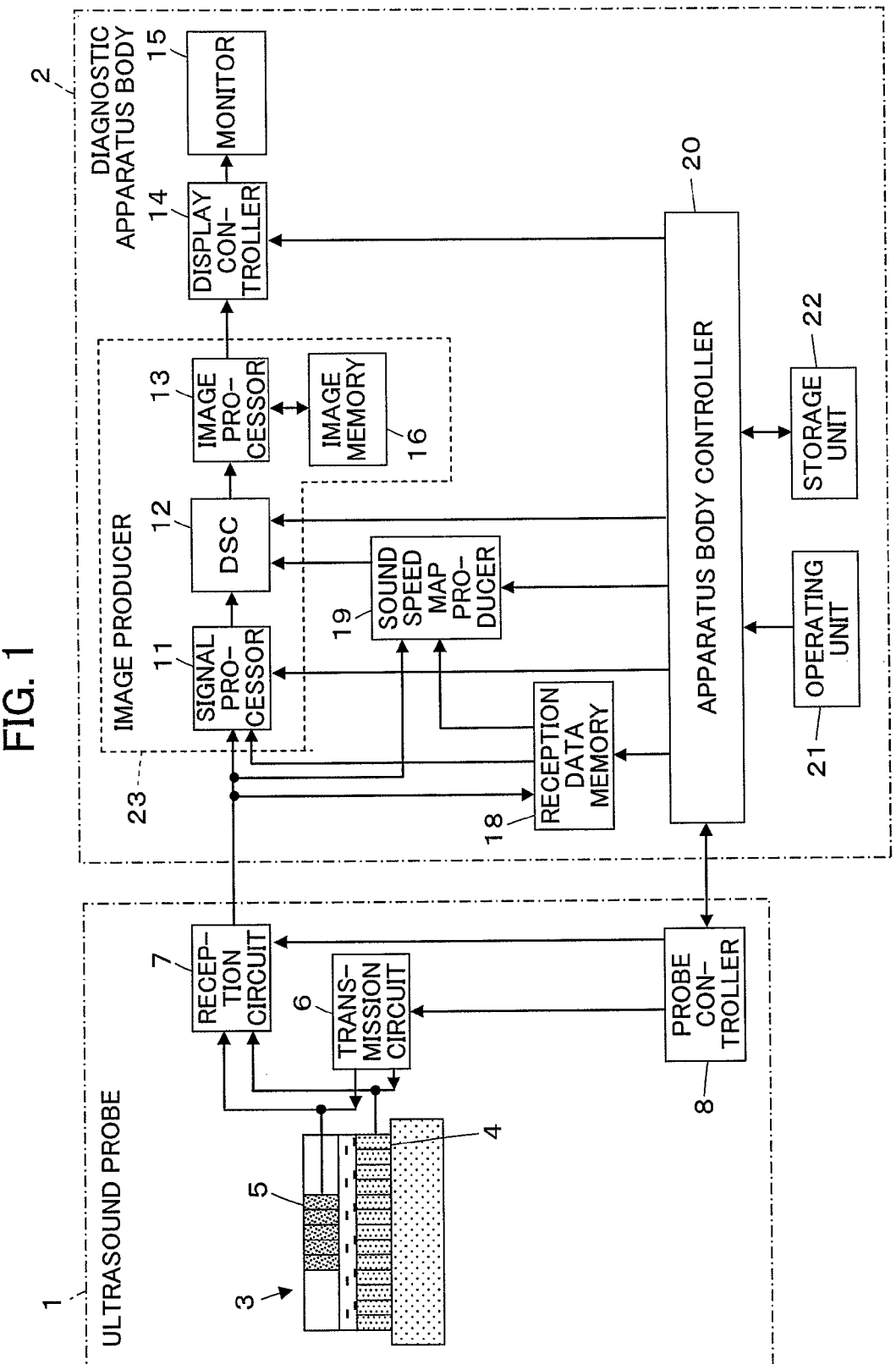
FIG. 1 is a block diagram showing the configuration of an ultrasound diagnostic apparatus including an ultrasound probe according to Embodiment 1 of the invention.

FIG. 1 shows the configuration of an ultrasound diagnostic apparatus including an ultrasound probe 1 according to Embodiment 1 of the invention. A diagnostic apparatus body 2 is connected to the ultrasound probe 1.

The ultrasound probe 1 has a laminated transducer array 3. The laminated transducer array 3 includes a transducer array 4 for a B-mode image and a transducer array 5 for sound speed measurement in a laminated state. A transmission circuit 6 and a reception circuit 7 are connected to the transducer array 4 for a B-mode image. The transmission circuit 6 and the reception circuit 7 are also connected to the transducer array 5 for sound speed measurement.

A probe controller 8 is connected to the transmission circuit 6 and the reception circuit 7.

The diagnostic apparatus body 2 has a signal processor 11 connected to the reception circuit 7 of the ultrasound probe 1, and a DSC (Digital Scan Converter) 12, an image processor 13, a display controller 14, and a monitor 15 are sequentially connected to the signal processor 11. An image memory 16 is connected to the image processor 13. The diagnostic apparatus body 2 has a reception data memory 18 and a sound speed map producer 19 each of which are connected to the reception circuit 7 of the ultrasound probe 1. An apparatus body controller 20 is connected to the signal processor 11, the DSC 12, the display controller 14, the reception data memory 18, and the sound speed map producer 19. An operating unit 21 and a storage unit 22 are connected to the apparatus body controller 20.

The probe controller 8 of the ultrasound probe 1 and the apparatus body controller 20 of the diagnostic apparatus body 2 are connected to each other.

The laminated transducer array 3 has the structure shown in FIG. 2. That is, the transducer array 4 for a B-mode image having a plurality of ultrasound transducers 4a arranged in a one-dimensional manner is formed on a backing member 31, and the transducer array 5 for sound speed measurement is laminated on the transducer array 4 for a B-mode image through a matching layer 32.

The transducer array 5 for sound speed measurement is formed in the central portion of another matching layer 33 formed on the matching layer 32. In order to limit the region where a sound speed map to a partial region with respect to a B-mode image, the transducer array 5 for sound speed measurement has a smaller number of ultrasound transducers 5a than the ultrasound transducers 4a in the transducer array 4 for a B-mode image. The array pitch P1 of the ultrasound transducers 5a of the transducer array 5 for sound speed measurement is equal to the array pitch of the ultrasound transducers 4a of the transducer array 4 for a B-mode image, and the transducer array 5 for sound speed measurement is located above the central portion of the transducer array 4 for a B-mode image.

The ultrasound transducers 4a of the transducer array 4 for a B-mode image transmit ultrasonic waves for B-mode image production in response to driving signals supplied from the transmission circuit 6, and the ultrasound transducers 5a of the transducer array 5 for sound speed measurement transmit ultrasonic waves for sound speed map production in response to driving signals supplied from the transmission circuit 6. The ultrasound transducers 4a of the transducer array 4 for a B-mode image receive an ultrasonic echo of the ultrasonic waves for B-mode image production by the subject and output reception signals to the reception circuit 7. The ultrasound transducers 5a of the transducer array 5 for sound speed measurement receive an ultrasonic echo of the ultrasonic waves for sound speed map production by the subject and output reception signals to the reception circuit 7.

Each ultrasound transducer 4a of the transducer array 4 for a B-mode image is constituted by a vibrator in which electrodes are formed at both ends of a piezoelectric body made of piezoelectric ceramic represented by PZT (Pb (lead) zirconate titanate) or piezoelectric single crystal represented by PMN-PT (lead magnesium niobate-lead titanate solid solution).

Each ultrasound transducer 5a of the transducer array 5 for sound speed measurement is constituted by a vibrator in which electrodes are formed at both ends of a piezoelectric body made of a polymer piezoelectric device represented by PVDF (polyvinylidene difluoride).

If a pulsed or continuous-wave voltage is applied across the electrodes of the vibrator, the piezoelectric body expands and contracts, thereby pulsed or continuous-wave ultrasonic waves are produced from the vibrators and synthesized to form an ultrasonic beam. When receiving the propagating ultrasonic waves, the vibrators expand and contract to produce electric signals, and the electric signals are output as the reception signals of the ultrasonic waves.

The transmission circuit 6 includes, for example, a plurality of pulsars. The transmission circuit 6 adjusts the delay amount of each of the driving signals on the basis of a transmission delay pattern selected in response to a control signal from the probe controller 8 such that ultrasonic waves transmitted from the ultrasound transducers 4a of the transducer array 4 for a B-mode image form an ultrasonic beam, and supplies the adjusted driving signals to the ultrasound transducers 4a. Simultaneously, the transmission circuit 6 adjusts the delay amount of each of the driving signals such that ultrasonic waves transmitted from the ultrasound transducers 5a of the transducer array 5 for sound speed measurement are focused on a point where sound speed should be measured, and supplies the adjusted driving signals to the ultrasound transducers 5a.

The reception circuit 7 amplifies the reception signals output from the ultrasound transducers 4a of the transducer array 4 for a B-mode image and the reception signals output from the ultrasound transducers 5a of the transducer array 5 for sound speed measurement, and performs A/D conversion for the amplified reception signals. The reception circuit 7, thereafter, performs a reception focus process by giving a delay to each of the reception signals in accordance with the distribution of sound speed set on the basis of a reception delay pattern selected in response to a control signal from the probe controller 8, and adding the reception signals. With this reception focus process, the focus of the ultrasonic echo is narrowed to produce reception data (sound ray signal).

The probe controller 8 controls the respective units of the ultrasound probe 1 on the basis of various control signals transmitted from the apparatus body controller 20 of the diagnostic apparatus body 2.

The signal processor 11 of the diagnostic apparatus body 2 corrects attenuation depending on the distance in accordance with the depth of the reflection position of the ultrasonic wave for reception data for a B-mode image produced by the reception circuit 7 of the ultrasound probe 1, and performs an envelope detection process to produce a B-mode image signal which is tomographic image information relating to the tissue of the subject.

The DSC 12 converts (raster-converts) the B-mode image signal produced by the signal processor 11 to an image signal based on a normal television signal scan system.

The image processor 13 performs various necessary image processes, such as a gradation process, on the B-mode image signal input from the DSC 12, and outputs the processed B-mode image signal to the display controller 14 or stores the processed B-mode image signal in the image memory 16.

The signal processor 11, the DSC 12, the image processor 13, and the image memory 16 form an image producer 23.

The display controller 14 displays an ultrasound diagnostic image on the monitor 15 on the basis of the B-mode image signal subjected to the image process by the image processor 13.

The monitor 15 includes, for example, a display device, such as an LCD, and displays the ultrasound diagnostic image under the control of the display controller 14.

The reception data memory 18 sequentially stores reception data output from the reception circuit 7 of the ultrasound probe 1. The reception data memory 18 also stores information (for example, parameters representing the depth of the reflection position of the ultrasonic wave, the density of the scan lines, and the width of the field of vision) relating to the frame rate input from the apparatus body controller 20 in association with reception data.

The sound speed map producer 19 calculates a local sound speed value in the tissue of the subject as a diagnosis target on the basis of reception data for sound speed measurement from among reception data stored in the reception data memory 18 under the control of the apparatus body controller 20, and produces a sound speed map.

The apparatus body controller 20 controls the respective units of the ultrasound diagnostic apparatus on the basis of a command input from the operating unit 21 by the operator.

The operating unit 21 is used when the operator performs an input operation, and may be constituted by a keyboard, a mouse, a trackball, a touch panel, or the like.

The storage unit 22 stores an operation program or the like, and may be constituted by, for example, a recording medium such as an MO, an MT, a RAM, a CD-ROM, a DVD-ROM, an SD card, a CF card, or a USB memory, or a server.

The signal processor 11, the DSC 12, the image processor 13, the display controller 14, and the sound speed map producer 19 are constituted by a CPU and an operation program which causes the CPU to perform various processes, and these may be constituted by digital circuits.

The operator can select one of the following three display modes by using the operating unit 21. That is, display can be performed in a desired mode from among a mode in which a B-mode image is displayed alone, a mode in which a sound speed map is displayed on a B-mode image in an overlapping manner (for example, display where color or luminance changes depending on a local sound speed value or display where points having the same local sound speed value are connected by a line), and a mode in which a B-mode image and a sound speed map image are displayed in parallel.

When displaying a B-mode image, first, ultrasonic waves are transmitted from the ultrasound transducers 4a of the transducer array 4 for a B-mode image in response to the driving signals from the transmission circuit 6 of the ultrasound probe 1, the reception signal from each ultrasound transducer 4a having received the ultrasonic echo from the subject is output to the reception circuit 7, and reception data is produced by the reception circuit 7. A B-mode image signal is produced by the signal processor 11 of the diagnostic apparatus body 2 to which reception data is input and is then raster-converted by the DSC 12, and various image processes are performed on the B-mode image signal in the image processor 13. Thereafter, an ultrasound diagnostic image is displayed on the monitor 15 on the basis of the B-mode image signal by the display controller 14.

The calculation of the local sound speed value may be performed by the method described in JP 2010-99452 A filed in the name of the applicant.

As shown in FIG. 3A, according to this method, when the ultrasonic waves are transmitted into the subject, a received wave Wx reaches the transducer array 5 from a lattice point X as a reflection point of the subject. Then, as shown in FIG. 3B, a plurality of lattice points A1, A2, . . . are arranged at regular intervals at positions shallower than the lattice point X, that is, at positions closer to the transducer array 5. Then, the local sonic speed at the lattice point X is obtained according to the Huygens principle whereby a synthesized wave Wsum of received waves W1, W2, . . . from a plurality of lattice points A1, A2, . . . having received the received wave from the lattice point X coincides with the received wave Wx from the lattice point X.

First, the optimum sound speed values for all the lattice points X, A1, A2, . . . are obtained. The optimum sound speed value is a speed sound value such that imaging is performed with focus calculation based on the set speed sound for each lattice point to form an ultrasound image, and when the set sound speed changes in various ways, contrast and sharpness of the image become highest. For example, as described in JP 8-317926 A, the optimum sound speed value can be determined on the basis of contrast of an image, a spatial frequency in a scan direction, dispersion, or the like.

Next, the waveform of a virtual received wave Wx emitted from the lattice point X is calculated using the optimum sound speed value for the lattice point X.

A virtual local sound speed value V at the lattice point X changes in various ways to calculate a virtual synthesized wave Wsum of the received waves W1, W2, . . . from the lattice points A1, A2, . . . . At this time, it is assumed that the sound speed is uniform in a region Rxa between the lattice point X and each of the lattice points A1, A2, . . . , and is equal to the local sound speed value V at the lattice point X. The time until the ultrasonic wave propagating from the lattice point X reaches the lattice points A1, A2, . . . becomes XA1/V, XA2/V, . . . , where XA1, XA2, . . . designate the distance between the respective lattice points A1, A2, . . . and the lattice point X, respectively. Accordingly, reflected waves emitted from the lattice points A1, A2, . . . with the delay of the time XA1/V, XA2/V, . . . are synthesized, thereby obtaining the virtual synthesized wave Wsum.

Next, deviations between a plurality of virtual synthesized waves Wsum calculated by changing the virtual local sound speed value V at the lattice point X and the virtual received wave Wx from the lattice point X are calculated, and the virtual local sound speed value V with the minimum deviation is determined to be the local sound speed value at the lattice point X. As the method of calculating the deviation between the virtual synthesized wave Wsum and the virtual received wave Wx from the lattice point X, a method in which an intercorrelation is made, a method in which phase matching addition is performed while the delay obtained from the synthesized wave Wsum is applied to the received wave Wx, a method in which phase matching addition is performed while the delay obtained from the received Wx is applied to the synthesized wave Wsum, or the like may be used.

In the above-described manner, it is possible to calculate the local speed sound value in the subject on the basis of reception data produced by the reception circuit 7 of the ultrasound probe 1 with high precision. Similarly, it is possible to produce the sound speed map which represents the distribution of the local sound speed values in the set region of interest.

Next, the operation of Embodiment 1 will be described.

First, an ultrasonic beam for a B-mode image is transmitted from the plurality of ultrasound transducers 4a of the transducer array 4 for a B-mode image in response to the driving signals from the transmission circuit 6 of the ultrasound probe 1, and a reception signal from each ultrasound transducer 4a having received an ultrasonic echo from the subject is output to the reception circuit 7 to produce reception data for a B-mode image. A B-mode image is displayed on the monitor 15 by the display controller 14 on the basis of the B-mode image signal produced by the image producer 23 of the diagnostic apparatus body 2.

If the operator operates the operating unit 21 to set a region of interest R on the B-mode image displayed on the monitor 15, a plurality of lattice points are set in the region R of interest by the apparatus body controller 20.

Next, the transmission circuit 6 and the reception circuit 7 are controlled by the probe controller 8, and transmission and reception of ultrasonic beams for sound speed measurement are sequentially performed while a transmission focus is formed at each of the plurality of lattice points set in the region of interest R. That is, an ultrasonic beam for sound speed measurement is transmitted from the plurality of ultrasound transducers 5a of the transducer array 5 for sound speed measurement in response to the driving signals from the transmission circuit 6 so as to form the focus at the lattice point in the region of interest R, and a reception signal from each ultrasound transducer 5a having received an ultrasonic echo from the subject is output to the reception circuit 7.

Each time an ultrasonic beam is received in such a manner, reception data for sound speed measurement produced by the reception circuit 7 is sequentially stored in the reception data memory 18. If reception data for sound speed measurement for all the lattice points in the region of interest R are acquired, a command to form a sound speed map is output from the apparatus body controller 20 to the sound speed map producer 19. The sound speed map producer 19 calculates the local sound speed value at each lattice point using reception data for sound speed measurement from among reception data stored in the reception data memory 18 to produce the sound speed map in the region of interest R. Data relating to the sound speed map obtained by the sound speed map producer 19 is raster-converted by the DSC 12, is subjected to various image processes by the image processor 13, and is then sent to the display controller 14. The B-mode image and the sound speed map are displayed on the monitor 15 in an overlapping manner or the B-mode image and the sound speed map image are displayed on the monitor 15 in parallel in accordance with the display mode input from the operating unit 21 by the operator.

Reception data for sound speed measurement produced by the reception circuit 7 is stored in the reception data memory 18 and also input to the signal processor 11 of the image producer 23. At this time, the actuation of the signal processor 11 is stopped in accordance with a command from the apparatus body controller 20, thereby preventing the B-mode image signal from being produced using reception data for sound speed measurement.

In this way, both production of a B-mode image and production of a sound speed map are performed. Since the laminated transducer array 3 is used in which the transducer array 5 for sound speed measurement is laminated and formed above the transducer array 4 for a B-mode image, it is possible to form the subject abutment portion of the ultrasound probe 1 in a small area, and to improve operational performance when the subject abutment portion of the ultrasound probe is pressed against the body surface of the subject to perform diagnosis while performing both production of a B-mode image and production of an accurate sound speed map.

Since the transducer array 5 for sound speed measurement is located above the central portion of the transducer array 4 for a B-mode image, driving signals with a small delay amount are simply supplied from the transmission circuit 6 to the plurality of ultrasound transducers 5a of the transducer array 5 for sound speed measurement, thereby forming a transmission focus at each lattice point in the region of interest R set on the B-mode image and more accurately performing sound speed measurement.

Since the ultrasound transducers 5a of the transducer array 5 for sound speed measurement are formed of polymer piezoelectric devices, it becomes possible to suppress the influence of side lobe, thereby improving resolution in the depth direction and the direction perpendicular to the depth direction.

A low-frequency ultrasonic beam may be transmitted from the transducer array 5 for sound speed measurement, and two or more harmonics may be received by the transducer array 5 for sound speed measurement, thereby highlighting side lobe and further reducing side lobe.

The number of ultrasound transducers 4a of the transducer array 4 for a B-mode image, the number of ultrasound transducers 5a of the transducer array 5 for sound speed measurement, the center frequency of the ultrasonic beam for a B-mode image, and the center frequency of the ultrasonic beam for sound speed measurement can be appropriately selected.

Although in Embodiment 1, in order to limit a region where a sound speed map is produced to a partial region with respect to a B-mode image, the number of ultrasound transducers 5a of the transducer array 5 for sound speed measurement is smaller than the number of ultrasound transducers 4a of the transducer array 4 for a B-mode image, the number of ultrasound transducers 5a of the transducer array 5 for sound speed measurement may be equal to the number of ultrasound transducers 4a of the transducer array 4 for a B-mode image, thereby producing a wider sound speed map.

Embodiment 2

Although in Embodiment 1 described above, the array pitch P1 of the ultrasound transducers 5a of the transducer array 5 for sound speed measurement is equal to the array pitch of the ultrasound transducers 4a of the transducer array 4 for a B-mode image, and the transducer array 5 for sound speed measurement is located on the central portion of the transducer array 4 for a B-mode image, the invention is not limited thereto. For example, as shown in FIG. 4, a smaller number of ultrasound transducers 34a than the number of ultrasound transducers 4a of the transducer array 4 for a B-mode image may be provided, and the array pitch P2 of the ultrasound transducers 34a may be set to a value greater than the array pitch P1 of the ultrasound transducers 4a in the transducer array 4 for a B-mode image, such that a transducer array 34 for sound speed measurement having the same length as the transducer array 4 for a B-mode image may be laminated and formed on the matching layer 32.

Even when such a laminated transducer array is used, as in Embodiment 1, it is possible to form the subject abutment portion of the ultrasound probe 1 in a small area, and to improve operational performance when the subject abutment portion of the ultrasound probe is pressed against the body surface of the subject to perform diagnosis while performing both production of a B-mode image and production of an accurate sound speed map.

Embodiment 3

Figure 5:
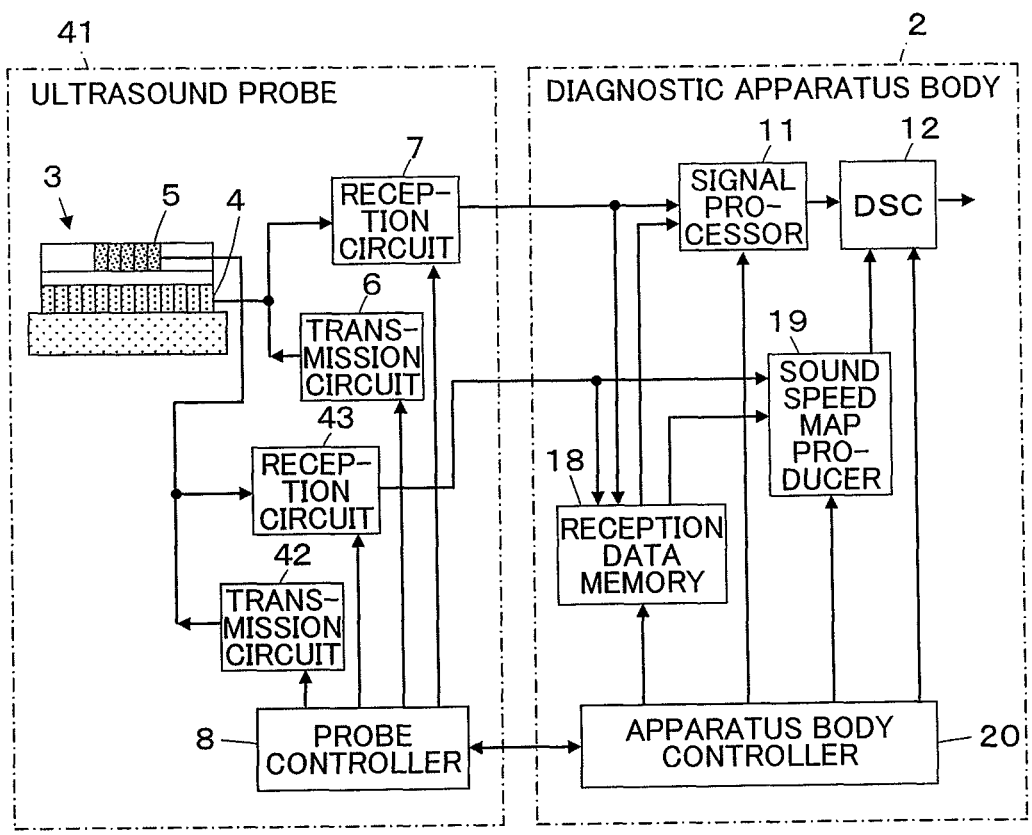
FIG. 5 is a block diagram showing the configuration of an ultrasound probe according to Embodiment 3.

FIG. 5 shows the configuration of an ultrasound probe 41 according to Embodiment 3. The ultrasound probe 41 uses the transmission circuit 6 and the reception circuit 7 in the ultrasound probe 1 of Embodiment 1 shown in FIG. 1 as dedicated transmission circuit and reception circuit for a B-mode image, and are also provided with dedicated transmission circuit 42 and reception circuit 43 for sound speed measurement are added. The transmission circuit 42 and the reception circuit 43 are connected to the transducer array 5 for sound speed measurement.

The dedicated reception circuit 43 for sound speed measurement is connected to the reception data memory 18 and the sound speed map producer 19 of the diagnostic apparatus body 2, and the dedicated reception circuit 7 for a B-mode image is connected to the signal processor 11 and the reception data memory 18 of the diagnostic apparatus body 2.

The transmission circuit 6 supplies driving signals to the transducer array 4 for a B-mode image to transmit an ultrasonic beam for a B-mode image from the transducer array 4 for a B-mode image, and the transmission circuit 42 supplies driving signals to the transducer array 5 for sound speed measurement to transmit an ultrasonic beam for sound speed measurement from the transducer array 5 for sound speed measurement.

The reception circuit 7 processes the reception signals output from the transducer array 4 for a B-mode image to produce reception data for a B-mode image and outputs reception data to the signal processor 11 and the reception data memory 18 of the diagnostic apparatus body 2. The reception circuit 43 processes the reception signals output from the transducer array 5 for sound speed measurement to produce reception data for sound speed measurement and outputs reception data to the reception data memory 18 and the sound speed map producer 19 of the diagnostic apparatus body 2.

With this configuration, transmission circuits and reception circuits appropriate for the transducer array 4 for a B-mode image having the ultrasound transducers 4*a* made of piezoelectric ceramic or the like and the transducer array 5 for sound speed measurement having the ultrasound transducers 5*a* made of polymer piezoelectric devices can be separately used. Since the number of ultrasound transducers 5*a* of the transducer array 5 for sound speed measurement is set to be smaller than the number of ultrasound transducers 4*a* of the transducer array 4 for a B-mode image, it is possible to simplify the internal configuration of the reception circuit 43 for sound speed measurement as much.

Although in Embodiments 1 to 3 described above, reception data output from the reception circuit 7 or 43 is temporarily stored in the reception data memory 18, and the sound speed map producer 19 produces a sound speed map in the region of interest R using reception data stored in the reception data memory 18, the sound speed map producer 19 may directly receive reception data output from the reception circuit 7 or 43 to produce a sound speed map.

The reception data memory 18 stores not only reception data for a sound speed map but also reception data for B-mode image production. For this reason, reception data for B-mode image production may be read from the reception data memory 18 as necessary under the control of the apparatus body controller 20, and a B-mode image may be generated by the image producer 23.

The connection of the ultrasound probe 1 or 41 and the diagnostic apparatus body 2 in Embodiments 1 to 3 described above may be either wired connection or connection by wireless communication.

What is claimed is:

1. An ultrasound probe which transmits an ultrasonic beam toward a subject and receives an ultrasonic echo by the subject, the ultrasound probe comprising:
   a transducer array for a B-mode image which has a plurality of ultrasound transducers and which transmits and receives an ultrasonic beam for a B-mode image; and
   a transducer array for sound speed measurement which is laminated and formed above the transducer array for a B-mode image and has a smaller number of ultrasound transducers than the plurality of ultrasound transducers of the transducer array for a B-mode image and which transmits and receives an ultrasonic beam for sound speed measurement,
   wherein an array pitch of the ultrasound transducers in the transducer array for sound speed measurement is equal to an array pitch of the ultrasound transducers in the transducer array for a B-mode image, and the transducer array for sound speed measurement is located above the central portion of the transducer array for a B-mode image.

2. The ultrasound probe according to claim 1,
   wherein the ultrasound transducers of the transducer array for sound speed measurement are constituted by polymer piezoelectric devices.

3. The ultrasound probe according to claim 1, further comprising:
   a transmission circuit which transmits the ultrasonic beam for a B-mode image from the transducer array for a B-mode image and transmits the ultrasonic beam for sound speed measurement from the transducer array for sound speed measurement; and
   a reception circuit which processes a reception signal based on the ultrasonic echo by the subject to obtain reception data for a B-mode image and reception data for a sound speed map.

4. The ultrasound probe according to claim 3,
   wherein the reception circuit includes a first reception circuit for a B-mode image which processes a reception signal output from the transducer array for a B-mode image to obtain reception data for a B-mode image, and a second reception circuit for sound speed measurement which processes a reception signal output from the transducer array for sound speed measurement to obtain reception data for sound speed measurement.

5. The ultrasound probe according to claim 3,
   wherein the transmission circuit includes a first transmission circuit for a B-mode image which transmits the ultrasonic beam for a B-mode image from the transducer array for a B-mode image, and a second transmission circuit which transmits the ultrasonic beam for sound speed measurement from the transducer array for sound speed measurement.

6. An ultrasound diagnostic apparatus comprising:
   the ultrasound probe according to claim 3;
   an image producer which produces a B-mode image on the basis of reception data for a B-mode image obtained by the reception circuit; and
   a sound speed map producer which produces a sound speed map on the basis of reception data for sound speed measurement obtained by the reception circuit.

7. An ultrasound probe which transmits an ultrasonic beam toward a subject and receives an ultrasonic echo by the subject, the ultrasound probe comprising:
   a transducer array for a B-mode image which has a plurality of ultrasound transducers and which transmits and receives an ultrasonic beam for a B-mode image; and
   a transducer array for sound speed measurement which is laminated and formed above the transducer array for a B-mode image and has a smaller number of ultrasound transducers than the plurality of ultrasound transducers of the transducer array for a B-mode image and which transmits and receives an ultrasonic beam for sound speed measurement,
   wherein an array pitch of the ultrasound transducers in the transducer array for sound speed measurement is greater than an array pitch of the ultrasound transducers in the transducer array for a B-mode image, and the transducer array for sound speed measurement has the same length as the transducer array for a B-mode image.

8. The ultrasound probe according to claim 7,
   wherein the ultrasound transducers of the transducer array for sound speed measurement are constituted by polymer piezoelectric devices.

9. The ultrasound probe according to claim 7, further comprising:
   a transmission circuit which transmits the ultrasonic beam for a B-mode image from the transducer array for a B-mode image and transmits the ultrasonic beam for sound speed measurement from the transducer array for sound speed measurement; and
a reception circuit which processes a reception signal based on the ultrasonic echo by the subject to obtain reception data for a B-mode image and reception data for a sound speed map.

10. The ultrasound probe according to claim 9, wherein the reception circuit includes a first reception circuit for a B-mode image which processes a reception signal output from the transducer array for a B-mode image to obtain reception data for a B-mode image, and a second reception circuit for sound speed measurement which processes a reception signal output from the transducer array for sound speed measurement to obtain reception data for sound speed measurement.

11. The ultrasound probe according to claim 9, wherein the transmission circuit includes a first transmission circuit for a B-mode image which transmits the ultrasonic beam for a B-mode image from the transducer array for a B-mode image, and a second transmission circuit which transmits the ultrasonic beam for sound speed measurement from the transducer array for sound speed measurement.

12. An ultrasound diagnostic apparatus comprising:
the ultrasound probe according to claim 9;
an image producer which produces a B-mode image on the basis of reception data for a B-mode image obtained by the reception circuit; and
a sound speed map producer which produces a sound speed map on the basis of reception data for sound speed measurement obtained by the reception circuit.

* * * * *